(12) United States Patent
Hasson et al.

(10) Patent No.: US 10,376,891 B2
(45) Date of Patent: Aug. 13, 2019

(54) SYSTEM AND METHOD FOR TEMPERATURE REFERENCING FOR MELT CURVE DATA COLLECTION

(71) Applicant: Canon U.S. Life Sciences, Inc., Rockville, MD (US)

(72) Inventors: Kenton C. Hasson, Germantown, MD (US); Hiroshi Inoue, Rockville, MD (US)

(73) Assignee: Canon U.S. Life Sciences, Inc., Rockville, MD (US)

(*) Notice: Subject to any disclaimer, the term of this patent is extended or adjusted under 35 U.S.C. 154(b) by 103 days.

(21) Appl. No.: 15/212,992

(22) Filed: Jul. 18, 2016

(65) Prior Publication Data

US 2016/0325285 A1 Nov. 10, 2016

Related U.S. Application Data

(62) Division of application No. 12/144,307, filed on Jun. 23, 2008, now Pat. No. 9,393,566.

(51) Int. Cl.
*C12Q 1/6813* (2018.01)
*B01L 7/00* (2006.01)
*C12Q 1/68* (2018.01)
*B01L 3/00* (2006.01)
*G01N 25/48* (2006.01)
(Continued)

(52) U.S. Cl.
CPC ............ *B01L 7/52* (2013.01); *B01L 3/502784* (2013.01); *C12Q 1/68* (2013.01); *C12Q 1/6825* (2013.01); *G01N 21/6428* (2013.01); *G01N 25/4866* (2013.01); *G01N 25/4893* (2013.01); *B01L 3/5025* (2013.01); *B01L 2200/147* (2013.01); *B01L 2300/0627* (2013.01); *B01L 2300/0816* (2013.01); *B01L 2300/1827* (2013.01); *G01N 21/645* (2013.01); *G01N 2021/6439* (2013.01); *G01N 2201/06113* (2013.01)

(58) Field of Classification Search
None
See application file for complete search history.

(56) References Cited

U.S. PATENT DOCUMENTS 5,683,657 A 11/1997 Mian
5,721,123 A 2/1998 Hayes et al.
(Continued)

FOREIGN PATENT DOCUMENTS

JP 2002-122488 A 4/2002
JP 2007-327927 A 12/2007
(Continued)

OTHER PUBLICATIONS

Lagally et al. "Single-Molecule DNA Amplification and Analysis in an Integrated Microfluidic Device," Analytical Chemistry 73:565-570 (2001).
(Continued)

*Primary Examiner* — Robert T. Crow
(74) *Attorney, Agent, or Firm* — Rothwell, Figg, Ernst & Manbeck, P.C.

(57) ABSTRACT

The present invention relates to systems and methods of temperature referencing for melt curve data collection. More specifically, the present invention relates to systems and methods for collecting DNA melt curve data for a DNA sample and a temperature reference material.

24 Claims, 6 Drawing Sheets

(51) Int. Cl.
*C12Q 1/6825* (2018.01)
*G01N 21/64* (2006.01)

(56) References Cited

U.S. PATENT DOCUMENTS

| | | | |
|---|---|---|---|
| 5,849,035 A | 12/1998 | Pathak et al. | |
| 6,030,115 A | 2/2000 | Ishiguro et al. | |
| 6,106,777 A | 8/2000 | Fujita et al. | |
| 6,149,787 A | 11/2000 | Chow et al. | |
| 6,238,869 B1 | 5/2001 | Kris et al. | |
| 6,267,858 B1 | 7/2001 | Parce et al. | |
| 6,274,337 B1 | 8/2001 | Parce et al. | |
| 6,288,220 B1 | 9/2001 | Kambara et al. | |
| 6,306,659 B1 | 10/2001 | Parce et al. | |
| 6,399,389 B1 | 6/2002 | Parce et al. | |
| 6,413,782 B1 | 7/2002 | Parce et al. | |
| 6,429,025 B1 | 8/2002 | Parce et al. | |
| 6,447,661 B1 | 9/2002 | Chow et al. | |
| 6,479,299 B1 | 11/2002 | Parce et al. | |
| 6,558,960 B1 | 5/2003 | Parce et al. | |
| 6,630,353 B1 | 10/2003 | Parce et al. | |
| 6,632,655 B1 | 10/2003 | Mehta et al. | |
| 6,635,427 B2 | 10/2003 | Wittwer et al. | |
| 6,670,153 B2 | 12/2003 | Stern | |
| 6,750,661 B2 | 6/2004 | Brooks et al. | |
| 6,951,632 B2 | 10/2005 | Unger et al. | |
| 6,967,489 B2 | 11/2005 | Brooks et al. | |
| 6,977,163 B1 | 12/2005 | Mehta | |
| 7,067,263 B2 | 6/2006 | Parce et al. | |
| 7,091,048 B2 | 8/2006 | Parce et al. | |
| 9,393,566 B2 * | 7/2016 | Hasson | B01L 3/502784 |
| 2001/0039014 A1 | 11/2001 | Bass et al. | |
| 2002/0117517 A1 | 8/2002 | Unger et al. | |
| 2002/0119536 A1 | 8/2002 | Stern | |
| 2003/0012692 A1 | 1/2003 | Lemee et al. | |
| 2003/0021725 A1 | 1/2003 | Unno et al. | |
| 2003/0022177 A1 | 1/2003 | Wittwer et al. | |
| 2003/0054383 A1 | 3/2003 | Bass et al. | |
| 2003/0054384 A1 | 3/2003 | Bass et al. | |
| 2003/0064393 A1 | 4/2003 | Bass et al. | |
| 2003/0094953 A1 | 5/2003 | Brooks et al. | |
| 2004/0033518 A1 | 2/2004 | Wittwer et al. | |
| 2004/0081997 A1 | 4/2004 | Stern | |
| 2004/0096960 A1 | 5/2004 | Burd Mehta et al. | |
| 2004/0227529 A1 | 11/2004 | Brooks et al. | |
| 2004/0238052 A1 | 12/2004 | Karp et al. | |
| 2005/0042639 A1 | 2/2005 | Knapp et al. | |
| 2005/0153318 A1 | 7/2005 | Schena | |
| 2005/0161335 A1 | 7/2005 | Liu et al. | |
| 2005/0202470 A1 | 9/2005 | Sundberg et al. | |
| 2005/0221329 A1 | 10/2005 | Kay | |
| 2005/0224351 A1 | 10/2005 | Unger et al. | |
| 2005/0233335 A1 | 10/2005 | Wittwer et al. | |
| 2006/0019253 A1 | 1/2006 | Wittwer et al. | |
| 2006/0024690 A1 | 2/2006 | Kao et al. | |
| 2006/0096691 A1 | 5/2006 | Bossi et al. | |
| 2006/0205061 A1 | 9/2006 | Roukes | |
| 2006/0238763 A1 | 10/2006 | Sarvazyan et al. | |
| 2006/0246493 A1 | 11/2006 | Jensen et al. | |
| 2006/0246501 A1 | 11/2006 | Northrup | |
| 2006/0257893 A1 | 11/2006 | Takahashi et al. | |
| 2007/0026421 A1 | 2/2007 | Sundberg et al. | |
| 2008/0003588 A1 | 1/2008 | Hasson et al. | |

FOREIGN PATENT DOCUMENTS

| | | |
|---|---|---|
| JP | 2008-502027 A | 1/2008 |
| WO | 2005/075683 A1 | 8/2005 |
| WO | 2005/121864 A2 | 12/2005 |
| WO | 2007/092643 A2 | 8/2007 |
| WO | 2008/005241 A2 | 1/2008 |
| WO | 2008/005246 A2 | 1/2008 |

OTHER PUBLICATIONS

Kopp et al., "Chemical Amplification: Continuous-Flow PCR on a Chip," Science 280:1046-1048 (1998).

Park et al., "Cylindrical Compact Thermal-Cycling Device for Continuous-Flow Polymerase Chain Reaction," Analytical Chemistry 75:6029-6033 (2003).

Ririe et al., "Product Differentiation by Analysis of DNA Melting Curves During hte Polymerase Chain Reaction," Analytical Biochemistry 245:154-160 (1997).

Wittwer et al. "High Resolution Genotyping by Amplicon Melting Analysis using LC Green" Clinical Chemistry 49:853-860 (2003).

Liew et al. "Genotyping of Single-Nucleotide Polymorphisms by High Resolution Melting of Small Amplicons" Clinical Chemistry 50(7):1156-1164 (2004).

Herrmann et al. "Amplicon DNA Melting Analysis for Mutation Scanning and Genotyping: Cross-Platform Comparison of Instruments and Dyes" Clinical Chemistry 52(3):494-503 (2006).

Liew, et al., "Closed-Tube SNP Genotyping Without Labeled Probes / A Comparison Between Unlabeled Probe and Amplicon Melting," American Journal of Clinical Pathology 127:341-348 (2007).

Liu, et al., "A nanoliter rotary device for polymerase chain reaction," Electrophoresis 23:1531-1536 (2002).

Dodge, et al., "A Microfluidic Platform Using Molecular Beacon-Based Temperature Calibration for Thermal Dehybridization of Surface-Bound DNA," Analytical Chemistry 76:1778-1787 (2004).

The definition of "bracket" provided by the online dictionary at wordsmith.net [retrieved on Oct. 28, 2010]. Retrieved from the Internet: <URL: www.wordsmyth.net/?ent=bracket#t_7>.

The definition of "bracket" provided by the online dictionary at merriam-webster.com [retrieved on Oct. 20, 2011]. Retrieved from the Internet: <URL: www.merriam-webser.com/dictionary/bracket>.

The definition of "bracket" provided by the online dictionary at merriam-webster.com [retrieved on Oct. 20, 2011]. Retrieved from the Internet: <URL: unabridged.merriam.webster.com/cgi-bin/Third>).

* cited by examiner

SYSTEM AND METHOD FOR TEMPERATURE REFERENCING FOR MELT CURVE DATA COLLECTION

CROSS REFERENCE OF RELATED APPLICATION

This application is a divisional of U.S. patent application Ser. No. 12/144,307, filed on Jun. 23, 2008, which is incorporated herein by reference in its entirety.

BACKGROUND

Field of the Invention

The present invention relates to systems and methods of temperature referencing for melt curve data collection. More specifically, the present invention relates to systems and methods for collecting DNA melt curve data for a DNA sample and a temperature reference material.

Description of Related Art

The detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, is ubiquitous technology for disease diagnosis and prognosis, marker assisted selection, correct identification of crime scene features, the ability to propagate industrial organisms and many other techniques. Determination of the integrity of a nucleic acid of interest can be relevant to the pathology of an infection or cancer. One of the most powerful and basic technologies to detect small quantities of nucleic acids is to replicate some or all of a nucleic acid sequence many times, and then analyze the amplification products. PCR is perhaps the most well-known of a number of different amplification techniques.

PCR is a powerful technique for amplifying short sections of DNA. With PCR, one can quickly produce millions of copies of DNA starting from a single template DNA molecule. PCR includes a three phase temperature cycle of denaturation of DNA into single strands, annealing of primers to the denatured strands, and extension of the primers by a thermostable DNA polymerase enzyme. This cycle is repeated so that there are enough copies to be detected and analyzed. In principle, each cycle of PCR could double the number of copies. In practice, the multiplication achieved after each cycle is always less than 2. Furthermore, as PCR cycling continues, the buildup of amplified DNA products eventually ceases as the concentrations of required reactants diminish. For general details concerning PCR, see Sambrook and Russell, *Molecular Cloning—A Laboratory Manual* (3rd Ed.), Vols. 1-3, Cold Spring Harbor Laboratory, Cold Spring Harbor, N.Y. (2000); *Current Protocols in Molecular Biology*, F. M. Ausubel et al., eds., Current Protocols, a joint venture between Greene Publishing Associates, Inc. and John Wiley & Sons, Inc., (supplemented through 2005) and *PCR Protocols A Guide to Methods and Applications*, M. A. Innis et al., eds., Academic Press Inc. San Diego, Calif. (1990).

Real-time PCR refers to a growing set of techniques in which one measures the buildup of amplified DNA products as the reaction progresses, typically once per PCR cycle. Monitoring the accumulation of products over time allows one to determine the efficiency of the reaction, as well as to estimate the initial concentration of DNA template molecules. For general details concerning real-time PCR see *Real-Time PCR: An Essential Guide*, K. Edwards et al., eds., Horizon Bioscience, Norwich, U.K. (2004).

More recently, a number of high throughput approaches to performing PCR and other amplification reactions have been developed, e.g., involving amplification reactions in microfluidic devices, as well as methods for detecting and analyzing amplified nucleic acids in or on the devices. Thermal cycling of the sample for amplification is usually accomplished in one of two methods. In the first method, the sample solution is loaded into the device and the temperature is cycled in time, much like a conventional PCR instrument. In the second method, the sample solution is pumped continuously through spatially varying temperature zones. See, for example, Lagally et al. (*Anal Chem* 73:565-570 (2001)), Kopp et al. (*Science* 280:1046-1048 (1998)), Park et al. (*Anal Chem* 75:6029-6033 (2003)), Hahn et al. (WO 2005/075683), Enzelberger et al. (U.S. Pat. No. 6,960,437) and Knapp et al. (U.S. Patent Application Publication No. 2005/0042639).

Microfluidic systems are systems that have at least one channel through which a fluid may flow, which channel has at least one internal cross-sectional dimension, (e.g., depth, width, length, diameter) that is less than about 1000 micrometers. Typically, microchannels have a cross-sectional dimension of about 5 microns to about 500 microns and a depth of about 1 micron to about 100 microns.

Melt curve analysis is an important technique for analyzing nucleic acids. In this method, a double stranded nucleic acid is denatured in the presence of a dye that indicates whether the two strands are bound or not. Examples of such indicator dyes include non-specific binding dyes such as SYBR® Green I, whose fluorescence efficiency depends strongly on whether it is bound to double stranded DNA. As the temperature of the mixture is raised, a reduction in fluorescence from the dye indicates that the nucleic acid molecule has melted, i.e., unzipped, partially or completely. Thus, by measuring the dye fluorescence as a function of temperature, information is gained regarding the length of the duplex, the GC content or even the exact sequence. See, for example, Ririe et al. (*Anal Biochem* 245:154-160, 1997), Wittwer et al. (*Clin Chem* 49:853-860, 2003), Liew et al. (*Clin Chem* 50:1156-1164 (2004), Herrmann et al. (*Clin Chem* 52:494-503, 2006), Knapp et al. (U.S. Patent Application Publication No. 2002/0197630), Wittwer et al. (U.S. Patent Application Publication No. 2005/0233335), Wittwer et al. (U.S. Patent Application Publication No. 2006/0019253) and Sundberg et al. (U.S. Patent Application Publication No. 2007/0026421).

A number of commercial instruments exist that perform thermal melts on DNA. Examples of available instruments include the Idaho Technology HR-1 high resolution melter and the Idaho Technology LightScanner high resolution melter. The HR-1 high resolution melter has the highest resolution fluorescent signal to noise ratio and temperature resolution of any commercial device. However, it suffers from a limitation that it can only analyze one sample at a time, and the sample container must be replaced manually. Replacement of the container for each test perhaps contributes to run-to-run temperature variability. The LightScanner high resolution melter also has good signal and temperature resolution, and operates on a 96-well plate sample container. However, it suffers from significant (~0.3° C.) temperature gradients across the entire plate, as do other systems based on standard well plates. A typical mode of operation for these analyzers is to apply heat to the sample(s) in a controlled manner to achieve a linear rise in temperature versus time. Simultaneously, a stable continuous fluorescence excitation light is applied, and emitted fluorescence is collected continuously over fixed integration time intervals. The fluorescence intensity data is converted from a time basis to a temperature basis based on the knowledge of the temperature ramp versus time.

One of the difficulties inherent to this method is that the temperature control system has limited precision and accuracy. For example, the feedback signal used to control the heater may come from a temperature sensor that is physically displaced from the sample. During a temperature ramp, heat diffuses from the heat source to the sample through the sample container, and hence temperature gradients exist within the sample and across the sample container as well. A temperature sensor outside the sample container, even if perfectly accurate, will report a temperature that is offset somewhat from the instantaneous sample temperature. Furthermore, this offset will depend upon the ramp rate, the geometry and the quality of thermal contact between the heater and the sample container.

There is current market interest in further developing microfluidic genomic sample analysis systems for detecting and analyzing DNA sequences. The development of these microfluidic systems often entail the various combinations of channel configurations, inlets, outlets, buffer insertion methods, boluses of genomic sample insertion methods, temperature cycling and control methods, and optical analysis methods. There is also further interest in developing systems and methods for temperature referencing for melt curve data collection.

Microfluidic melting curve analysis is typically carried out either in a stopped flow format or in a continuous flow format. In a stopped flow format, flow is stopped within a microchannel of a microfluidic device while the temperature in that channel is ramped through a range of temperatures required to generate the desired melt curve. A drawback to the stopped flow format is that it does not integrate well in systems with other flow through processes which require the flow to continue without any stoppage. When fluorescent indicator dyes are used to monitor denaturation, another drawback to the stopped flow format is the loss of fluorescent signal due to dye photobleaching while the thermal ramp is being performed.

In a continuous flow format, a melting curve analysis is performed by applying a temperature gradient along the length (direction of flow) of a microchannel in a microfluidic device. If the melting curve analysis requires that the molecules being analyzed be subjected to a range of temperatures extending from a first temperature to a second temperature, the temperature at one end of the microchannel is controlled to the first temperature, and the temperature at the other end of the length is controlled to the second temperature, thus creating a continuous temperature gradient spanning the temperature range between the first and second selected temperatures. A drawback to certain implementations of the continuous flow format is that thermal properties of the molecules in the stream must be measured at multiple points along the temperature gradient to generate the desired melting curve. This makes measurement of thermal properties of the molecules in the stream more complex than in the stopped flow format, where thermal properties of the molecules in the stream can be measured at a single point to generate the desired melting curve.

Sundberg et al. (U.S. Patent Application Publication No. 2007/0026421) and Knight et al. (U.S. Patent Application Publication No. 2007/0231799), each incorporated by reference herein, describe methods, systems, kits and devices for conducting binding assays using molecular melt curves in microfluidic devices. Molecule(s) to be assayed can be flowed through microchannels in the devices where the molecule(s) optionally are exposed to additional molecules constituting, e.g., fluorescence indicator molecules and/or binding partners of the molecule being assayed. The molecules involved are then heated (and/or cooled) and a detectable property of the molecules is measured over a range of temperatures. From the resulting data, a thermal property curve(s) is constructed which allows determination and quantification of the binding affinity of the molecules involved.

Known systems and methods for melt curve analysis suffer from some amount of uncertainty and lack of reproducibility, inter alia, in terms of temperature control and measurement systems. Accordingly, there is a continuing need to improve the usefulness of the melt curve analysis technique by reducing the impact of spatial and temporal temperature fluctuations.

SUMMARY OF THE INVENTION

The present invention relates to systems and methods of temperature referencing for melt curve data collection. More specifically, the present invention relates to systems and methods for collecting DNA melt curve data for a DNA sample and a temperature reference material.

Thus, in a first aspect, the present invention provides a system for performing melt curve data collection comprising a container, a heating system and a detection system, wherein the container comprises at least two chambers that are in close thermal connection and wherein at least one chamber contains a DNA sample to be tested and at least one chamber contains a temperature reference material. In some embodiments, the heating system supplies heat to all of the chambers simultaneously. In some embodiments, the chambers contain at least two spatially separated temperature reference materials to determine a spatial temperature gradient. In other embodiments, the temperature reference materials bracket the DNA sample in both space and time. In further embodiments, the temperature reference material is mixed with the DNA sample. In some embodiments, the detection system is an optical detection system. In other embodiments, detectable signal from the temperature reference material provides feedback to the heating system. In further embodiments, the container is a microfluidic chip and the chambers are microfluidic channels in the chip. In some embodiments, the container comprises at least three chambers wherein at least two of the chambers are spatially separated from each other and contain a temperature reference material to determine a spatial temperature gradient. In other embodiments, at least two chambers containing DNA samples are located between two chambers containing the temperature reference material. In some embodiments, the temperature reference material is a known DNA mixture. In other embodiments, the temperature reference material is a thermochromatic material.

In a second aspect, the present invention provides a system for performing melt curve data collection comprising a container, a heating system and a detection system, wherein the container comprises at least one chamber that is refillable without moving the container, wherein the container contains a DNA sample to be tested and a temperature reference material. In some embodiments, the heating system supplies heat to all of the chambers simultaneously. In some embodiments, the detection system is an optical detection system. In other embodiments, detectable signal from the temperature reference material provides feedback to the heating system. In some embodiments, the DNA sample and the temperature reference material are alternated in the chamber. In other embodiments, the temperature reference material brackets the DNA sample in both space and time. In further embodiments, the DNA sample and the temperature reference material are mixed, wherein the temperature reference material has a detection signature that is discernible from that of the DNA sample and wherein data from both the sample and the temperature reference material are collected at the same place and the same time. In some embodiments, the temperature reference material is also a flow marker.

In some embodiments, the container is a microfluidic chip and the chambers are microfluidic channels in the chip. In some embodiments, the container comprises at least three chambers wherein at least two of the chambers are spatially separated from each other and contain a temperature reference material to determine a spatial temperature gradient. In other embodiments, at least two chambers containing DNA samples are located between two chambers containing the temperature reference material. In some embodiments, the temperature reference material is a known DNA mixture. In other embodiments, the temperature reference material is a thermochromatic material.

In a third aspect, the present invention provides a method of performing melt curve data collection comprising providing a container which includes at least two chambers that are in close thermal connection, introducing a DNA sample to be tested into at least one of the chambers and a temperature reference material into at least one of the other chambers, heating the chambers from a first temperature to a second temperature, and measuring a detectable property emanating from the DNA sample and a detectable property emanating from the temperature reference material, wherein the detectable property of the DNA sample indicates an extent of denaturation of the DNA in the sample and the detectable property of the temperature reference material is correlated to the temperature. In some embodiments, the chambers contain at least two spatially separated temperature reference materials and the detectable property emanating from the temperature reference materials is measured to determine a spatial temperature gradient. In other embodiments, the temperature reference materials bracket the DNA sample in both space and time. In some embodiments, the detectable property emanating from the temperature reference materials bracketing the DNA sample is measured to determine a spatial temperature gradient and any temporal fluctuation. In further embodiments, the temperature reference material is mixed with the DNA sample.

In some embodiments, the detectable property is measured with an optical detection system. In other embodiments, detectable signal from the temperature reference material provides feedback to the heating system. In further embodiments, the container is a microfluidic chip and the chambers are microfluidic channels in the chip. In some embodiments, the container comprises at least three chambers wherein at least two of the chambers are spatially separated from each other and contain temperature reference materials and the detectable property emanating from the temperature reference materials is measured to determine a spatial temperature gradient. In other embodiments, at least two chambers containing DNA samples are located between two chambers containing the temperature reference material. In some embodiments, the temperature reference material is a known DNA mixture. In other embodiments, the temperature reference material is a thermochromatic material.

In a fourth aspect, the present invention provides a method of performing melt curve data collection comprising providing a container which includes at least one chamber that is refillable without moving the container, introducing a DNA sample to be tested into at least one of the chambers and a temperature reference material into at least one of the chambers, heating the chambers from a first temperature to a second temperature, and measuring a detectable property emanating from the DNA sample and a detectable property emanating from the temperature reference material, wherein the detectable property of the DNA sample indicates an extent of denaturation of the DNA and the detectable property of the temperature reference material is correlated to the temperature.

In some embodiments, the detectable property is measured with an optical detection system. In other embodiments, detectable signal from the temperature reference material provides feedback to the heating system. In some embodiments, the DNA sample and the temperature reference material are alternated in the chamber. In other embodiments, wherein the temperature reference material brackets the DNA sample in both space and time. In some embodiments, the detectable property emanating from the temperature reference materials bracketing the DNA sample is measured to determine a spatial temperature gradient and any temporal fluctuation.

In further embodiments, the DNA sample and the temperature reference material are mixed, wherein the temperature reference material has a detection signature that is discernible from that of the DNA sample and wherein data from both the sample and the temperature reference material are collected at the same place and the same time. In some embodiments, the temperature reference material is also a flow marker. In some embodiments, the container is a microfluidic chip and the chambers are microfluidic channels in the chip. In some embodiments, the container comprises at least three chambers wherein at least two of the chambers are spatially separated from each other and contain temperature reference materials and the detectable property emanating from the temperature reference materials is measured to determine a spatial temperature gradient. In other embodiments, at least two chambers containing DNA samples are located between two chambers containing the temperature reference material. In some embodiments, the temperature reference material is a known DNA mixture. In other embodiments, the temperature reference material is a thermochromatic material.

The above and other embodiments of the present invention are described below with reference to the accompanying drawings.

BRIEF DESCRIPTION OF THE DRAWINGS

The accompanying drawings, which are incorporated herein and form part of the specification, illustrate various embodiments of the present invention. In the drawings, like reference numbers indicate identical or functionally similar elements.

DETAILED DESCRIPTION OF THE INVENTION

The present invention has several embodiments and relies on patents, patent applications and other references for details known to those of the art. Therefore, when a patent, patent application, or other reference is cited or repeated herein, it should be understood that it is incorporated by reference in its entirety for all purposes as well as for the proposition that is recited.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, N.Y., Gait, *Oligonucleotide Synthesis: A Practical Approach*, 1984, IRL Press, London, Nelson and Cox (2000), Lehninger, *Principles of Biochemistry* 3rd Ed., W. H. Freeman Pub., New York, N.Y. and Berg et al. (2002) *Biochemistry*, 5th Ed., W. H. Freeman Pub., New York, N.Y., all of which are herein incorporated in their entirety by reference for all purposes.

As described above, the known systems and methods for melt curve analysis suffer from some amount of uncertainty and lack of reproducibility, inter alia, in terms of temperature control and measurement systems. The present invention provides systems and methods for temperature referencing for melt curve data collection. The present invention provides improvements in melt curve analysis technique by reducing the impact of spatial and temporal temperature fluctuations.

Figure 1:
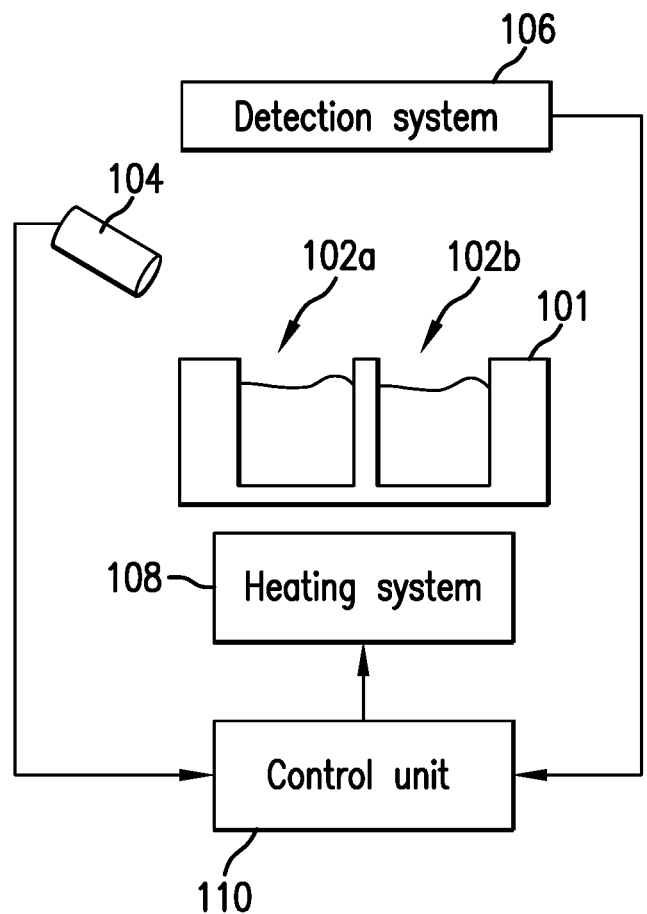
FIG. 1 is a diagram illustrating a system according to an embodiment of the present invention.

As shown in FIG. 1, an embodiment of the present invention provides a system for performing melt curve data collection comprising a container 101, a heating system 108 and a detection system 106. Container 101 comprises at least two chambers 102a and 102b. In one embodiment, the chambers have the same physical dimensions. In other embodiments, the chambers are located in close proximity to one another such that they are in close thermal connection. In some embodiments, the chambers are located less than 1 mm from each other. In other embodiments, the chambers are located less than 0.3 mm from each other. In some embodiments, heating system 108 supplies heat to all of the chambers simultaneously. In some embodiments, an optional temperature sensor monitors the container and provides feedback control to the heating system. In some embodiments, detection system 106 is an optical detection system. In other embodiments, detection system 106 monitors the optical properties (e.g., fluorescence emission) from the chambers simultaneously. The system may further comprise an excitation source 104 (e.g., a laser or other excitation source) for illuminating the chambers. Detection system 106 detects light (e.g., fluorescence or other light) that comes from the chambers after illumination by excitation source 104. The system may further comprise a control unit 110. Control unit 110 controls heating system 108 and may receive feedback from the heating system. In some embodiments, a detectable signal (e.g., fluorescence emission) received by the detection system 106 provides feedback to the heating system through control unit 110. In other embodiments, excitation source 104 provides feedback to the control unit 110 for controlling detection of the detectable signal by detection system 106.

In one embodiment, at least one chamber of the system contains a test sample of unknown DNA (i.e., DNA sample) to be tested (i.e., measured by melt curve analysis) and at least one chamber contains a temperature reference material. In some embodiments, the DNA sample comprises PCR amplicons. In other embodiments, the PCR amplicons contain a dsDNA binding dye. Suitable dsDNA binding dyes included SYBR® Green 1 (Invitrogen Corp., Carlsbad, Calif.), SYTO® 9 (Invitrogen Corp., Carlsbad, Calif.), LC Green® (Idaho Technologies, Salt Lake City, Utah) and Eva Green™ (Biotium Inc, Hayward, Calif.). In further embodiments, the DNA sample comprises an unlabeled probe and single stranded amplicon produced by asymmetric PCR. In some embodiments, the chambers contain at least two spatially separated temperature reference materials to determine a spatial temperature gradient. In other embodiments, the temperature reference materials bracket the DNA sample in both space and time. In further embodiments, the temperature reference material is mixed with the DNA sample. In this embodiment, the temperature reference material has a detection signature that is discernible from that of the DNA sample. In some embodiments, data from both the sample and the temperature reference material are collected at the same place and the same time.

In some embodiments, the container is a microfluidic chip and the chambers are microfluidic channels in the chip. In some embodiments, the container comprises at least three chambers wherein at least two of the chambers are spatially separated from each other and contain a temperature reference material to determine a spatial temperature gradient. In other embodiments, at least two chambers containing DNA samples are located between two chambers containing the temperature reference material.

Heating system 108 provides a substantially steadily increasing amount of heat to the chambers to cause the DNA present in the chamber(s) to melt (i.e., to cause the dsDNA in the chamber to transition to ssDNA) for the generation of a melt curve. In one example, heating system 108 may provide a thermal ramp rate of typically 0.1° C. to 2° C. per second, with the preferred ramp rate being between 0.5° C. and 1° C. per second. Typically, the temperature may increase from temperature t1 (e.g., about 65° C.) to temperature t2 (e.g., about 95° C.). In some embodiments, heating system 108 is configured to provide heat to and/or absorb heat from the chambers and, thus, may include one or more heat sources and/or heat sinks (e.g., heating system 108 may include a peltier device or other heat source or sink).

The temperature reference material is a known standard that exhibits a well-characterized and reproducible optical property change as a function of temperature. In some embodiments, the temperature reference material is a known DNA mixture. In some embodiments, the DNA mixture is a mixture of homogeneous short DNA duplexes with a known melting transition. In other embodiments, the DNA mixture is a mixture of DNA duplexes having more than one melting transition. In further embodiments, the DNA mixture is a mixture of longer DNA duplexes with multiple melting domains. In some embodiments, the temperature reference material is a thermochromatic material. In some embodiments, the thermochromatic material is a thermochromic leuco dye. In other embodiments, the thermochromatic material is a thermochromic liquid crystal material. Examples of thermochromic leuco dyes include, but are note limited to, spirolactones, fluorans, spiropyrans and fulgides. Examples of thermochromic liquid crystal materials include, but are not limited to cholesteryl nonanoate (also called cholesteryl pelargonate, 3β-cholest-5-en-3-ol nonanoate or cholest-5-ene-3-β-yl nonanoate) and cyanobiphenyls.

Figure 2:
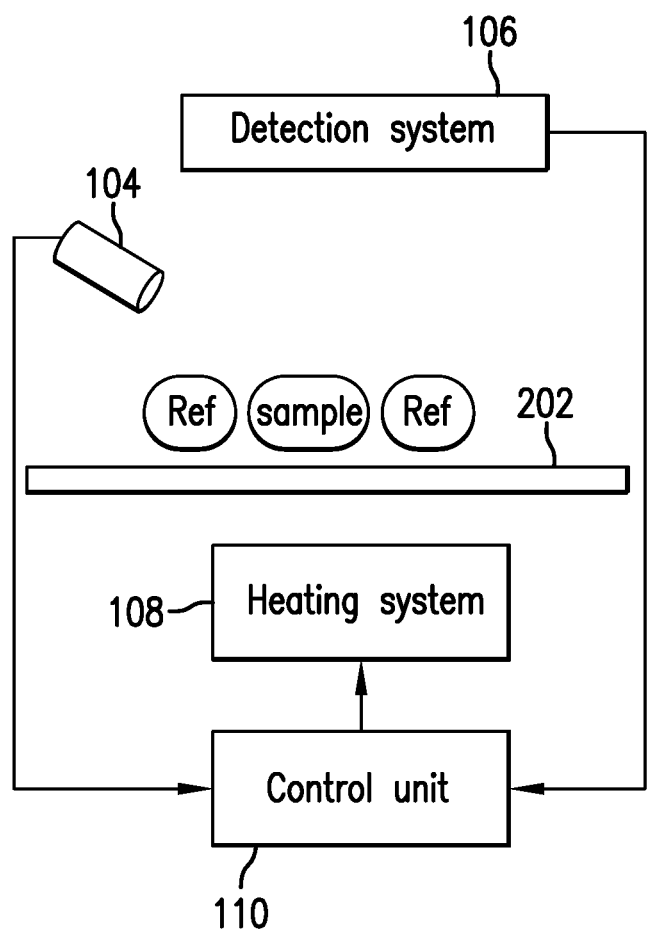
FIG. 2 is a diagram illustrating a system according to another embodiment of the present invention.

As shown in FIG. 2, the present invention provides a system for performing melt curve data collection comprising a container 202, a heating system 108 and a detection system 106. In this embodiment of the invention, container 202 comprises at least one chamber that is refillable without moving the container. Container 202 contains a DNA sample to be tested and a temperature reference material. In some embodiments, heating system 108 supplies heat to all of the chambers simultaneously. In some embodiments, an optional temperature sensor monitors the container and provides feedback control to the heating system. In some embodiments, detection system 106 is an optical detection system. In other embodiments, detection system 106 monitors the optical properties (e.g., fluorescence emission) from the chambers simultaneously. The system may further comprise an excitation source 104 (e.g., a laser or other excitation source) for illuminating the chambers. Detection system 106 detects light (e.g., fluorescence or other light) that comes from the chambers after illumination by excitation source 104. The system may further comprise a control unit 110. Control unit 110 controls heating system 108 and may receive feedback from the heating system. In some embodiments, a detectable signal (e.g., fluorescence emission) received by the detection system 106 provides feedback to the heating system through control unit 110. In other embodiments, excitation source 104 provides feedback to the control unit 110 for controlling detection of the detectable signal by detection system 106. Thus, this embodiment of the invention provides container 202 having chambers that can be emptied and refilled with new solutions without needing to physically remove and replace the entire sample container with respect to excitation source 104, detection system 106, heating system 108 and control unit 110.

In some embodiments, the DNA sample and the temperature reference material are alternated in the chamber within container 202. In other embodiments, the temperature reference material brackets the DNA sample in both space and time. An illustration of the temperature reference material bracketing the DNA sample is shown in FIG. 2. In further embodiments, the DNA sample and the temperature reference material are mixed. In this embodiment, the temperature reference material has a detection signature that is discernible from that of the DNA sample. In some embodiments, data from both the sample and the temperature reference material are collected at the same place and the same time. In some embodiments, the temperature reference material is also a flow marker for monitoring flow through the chamber.

In some embodiments, the container comprises at least three chambers wherein at least two of the chambers are spatially separated from each other and contain a temperature reference material to determine a spatial temperature gradient, such as illustrated in FIG. 2. In other embodiments, at least two chambers containing DNA samples are located between two chambers containing the temperature reference material. In some embodiments, the temperature reference material is a known DNA mixture, such as described herein. In other embodiments, the temperature reference material is a thermochromatic material, such as described herein.

Figure 3:
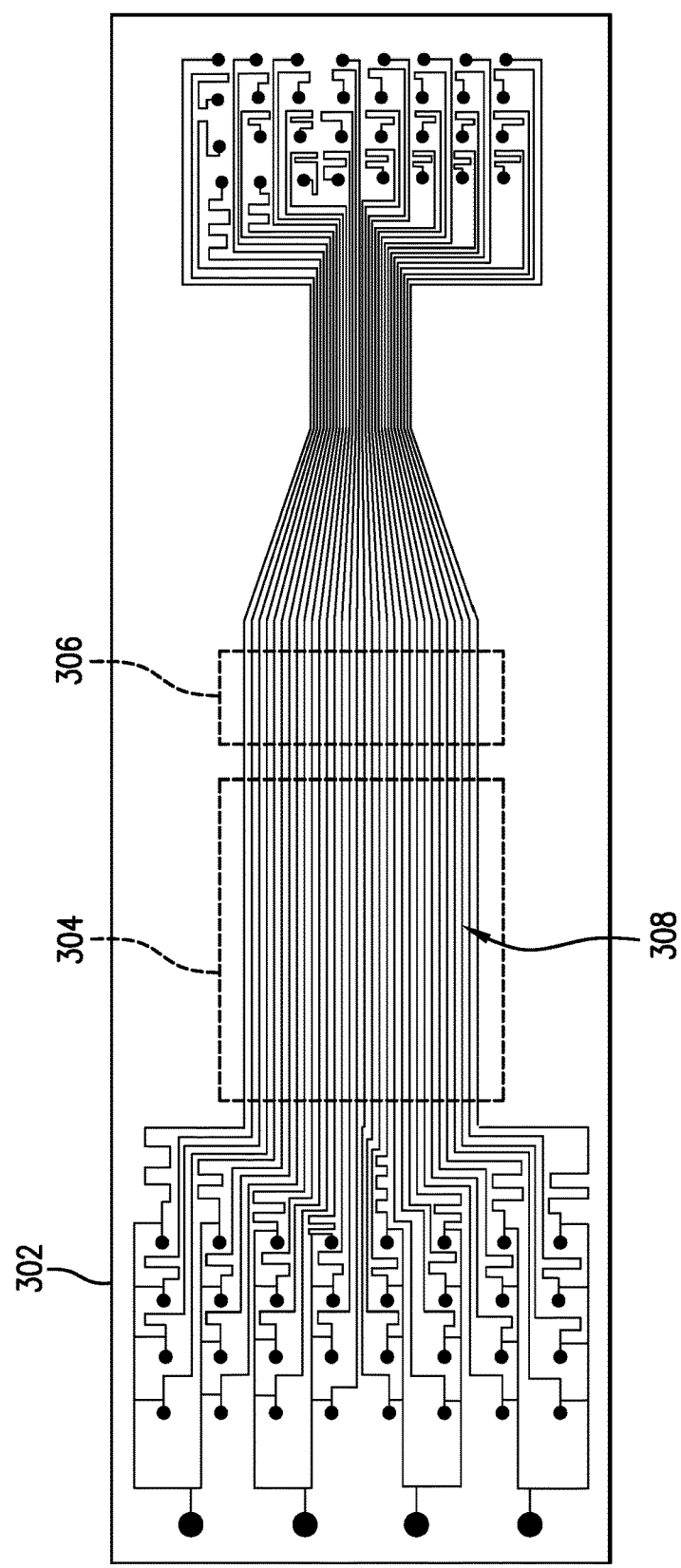
FIG. 3 shows a microfluidic device that is capable of performing melt curve data collection according to an embodiment of the present invention.

In some embodiments, such as shown in FIG. 3, the container is a microfluidic chip and the chambers are microfluidic channels in the chip. As shown in FIG. 3, chip 302 includes a number of microfluidic channels 308. In the example shown, there are 32 microfluidic channels, but it is contemplated that chip 302 may have more or less than 32 channels. As shown, a first portion of each microfluidic channel may be within a PCR processing zone 304 and a second portion of each microfluidic channel may be within a melt analysis zone 306. As further shown, zone 306 may immediately follow zone 304 and the length of zone 304 may be significantly greater than the length of zone 306. An example of a microfluidic chip that can be used in connection the present invention is described in U.S. Patent Application Publication No. 2008/0003593, incorporated herein by reference. An example of a system and method for performing PCR in a microfluidic chip is described in U.S. Patent Application Publication No. 2008/0003588, incorporated herein by reference. Other microfluidic chips are well known in the art.

The present invention also provides a method of performing melt curve data collection. In accordance with one aspect, the method comprises (a) providing a container which includes at least two chambers that are in close thermal connection, (b) introducing a DNA sample to be tested into at least one of the chambers and a temperature reference material into at least one of the other chambers, (c) heating the chambers from a first temperature to a second temperature, and (d) measuring a detectable property emanating from the DNA sample and a detectable property emanating from the temperature reference material. The detectable property of the DNA sample indicates an extent of the denaturation (i.e., melting) of the DNA in the sample. The detectable property of the temperature reference material is correlated to the temperature.

In one example, the DNA sample and the temperature reference material are as described herein. The chambers are heated in such a manner that a thermal ramp rate of typically 0.1° C. to 2° C. per second, with the preferred ramp rate being between 0.5° C. and 1° C. per second, is produced. Typically, the temperature may increase from temperature t1 (e.g., about 65° C.) to temperature t2 (e.g., about 95° C.).

In one embodiment, at least one of the chambers contains a temperature reference material. In this embodiment, melt data from the DNA sample and data from the temperature reference material are collected simultaneously as the temperature is ramped. Because the chambers are small and in close proximity, and the heater has been designed to supply heat uniformly, the temperature difference between the two chambers should be small. These two data sets are then compared to infer the actual melt properties of the DNA sample.

In some embodiments, the chambers contain at least two spatially separated temperature reference materials and the detectable property emanating from the temperature reference materials is measured to determine a spatial temperature gradient. In other embodiments, the temperature reference materials bracket the DNA sample in both space and time. In some embodiments, the detectable property emanating from the temperature reference materials bracketing the DNA sample is measured to determine a spatial temperature gradient and any temporal fluctuation. By having at least two spatially separated temperature references measured simultaneously, the temperature gradient can be measured and the data compensated to account for the gradient. For example, the temperature at the location of an unknown sample could be estimated by interpolating the results from temperature standards that surround that location.

In further embodiments, the temperature reference material is mixed with the DNA sample. This method could be the ultimate in accuracy because the temperature reference is measured in the same location and at the same time as the unknown sample. This method requires the use of a material whose optical property change with temperature is discernible from the melt-dependent fluorescence from the DNA/binding dye under test. There are a number of physical properties that could conceivably be measured including absorbance and luminescence the efficiency, wavelength, polarization, or lifetime of emitted fluorescence, absorbance vs. wavelength, birefringence, etc. The addition of the temperature standard would ideally not interfere with the DNA melt measurement in any way, i.e. it would not alter the melt properties, would not affect the measurement process, and also would preferably not interfere with PCR.

In some embodiments, the detectable property is measured with an optical detection system as described herein. In other embodiments, detectable signal from the temperature reference material provides feedback to the heating system. In further embodiments, the container is a microfluidic chip and the chambers are microfluidic channels in the chip. In some embodiments, the container comprises at least three chambers wherein at least two of the chambers are spatially separated from each other and contain temperature reference materials and the detectable property emanating from the temperature reference materials is measured to determine a spatial temperature gradient. In other embodiments, at least two chambers containing DNA samples are located between two chambers containing the temperature reference material. In some embodiments, the temperature reference material is a known DNA mixture, such as described herein. In other embodiments, the temperature reference material is a thermochromatic material, such as described herein.

In a second aspect, the method of the present invention comprises (a) providing a container which includes at least one chamber that is refillable without moving the container, (b) introducing a DNA sample to be tested into at least one of the chambers and a temperature reference material into at least one of the chambers, (c) heating the chambers from a first temperature to a second temperature, and (d) measuring a detectable property emanating from the DNA sample and a detectable property emanating from the temperature reference material. The detectable property of the DNA sample indicates an extent of denaturation (i.e., melting) of the DNA in the sample. The detectable property of the temperature reference material is correlated to the temperature.

In this aspect, new DNA samples and temperature reference material are simply pumped into the refillable chambers. There is no need to physically remove and replace the entire sample container with respect to the optical and temperature control systems. This attribute reduces the chance of run-to-run temperature fluctuations because the thermal properties of the container, as well as its contact with the heater (and additional temperature sensors), remains the same. In addition, the impact of temperature fluctuations is further reduced in this aspect because the method is capable of measuring the temperature reference standards in the same channel, by sequentially alternating the temperature reference materials with the unknown DNA samples. Analogous to the idea of bracketing the unknown samples in space at the same time, this idea is to bracket the unknown samples in time, at the same location.

In one example, the DNA sample and the temperature reference material are as described herein. The chambers are heated in such a manner that a thermal ramp rate of typically 0.1° C. to 2° C. per second, with the preferred ramp rate being between 0.5° C. and 1° C. per second, is produced. Typically, the temperature may increase from temperature t1 (e.g., about 65° C.) to temperature t2 (e.g., about 95° C.).

In some embodiments, the detectable property is measured with an optical detection system as described herein. In other embodiments, detectable signal from the temperature reference material provides feedback to the heating system. In some embodiments, the DNA sample and the temperature reference material are alternated in the chamber. In other embodiments, wherein the temperature reference material brackets the DNA sample in both space and time. In some embodiments, the detectable property emanating from the temperature reference materials bracketing the DNA sample is measured to determine a spatial temperature gradient and any temporal fluctuation.

In further embodiments, the DNA sample and the temperature reference material are mixed, wherein the temperature reference material has a detection signature that is discernible from that of the DNA sample and wherein data from both the sample and the temperature reference material are collected at the same place and the same time. In some embodiments, the temperature reference material is also a flow marker. In some embodiments, the container is a microfluidic chip and the chambers are microfluidic channels in the chip. In some embodiments, the container comprises at least three chambers wherein at least two of the chambers are spatially separated from each other and contain temperature reference materials and the detectable property emanating from the temperature reference materials is measured to determine a spatial temperature gradient. In other embodiments, at least two chambers containing DNA samples are located between two chambers containing the temperature reference material. In some embodiments, the temperature reference material is a known DNA mixture. In other embodiments, the temperature reference material is a thermochromatic material.

An example of a container with refillable chambers is a microfluidic chip containing channels or a microcapillary system. New DNA sample boluses and temperature reference material boluses are simply pumped into the melt detection region, without moving the container. This attribute reduces the chance of run-to-run temperature fluctuations because the thermal properties of the container, as well as its contact with the heater (and additional temperature sensors), remains the same. To further reduce the impact of temperature fluctuations, this embodiment is capable of measuring the temperature reference standards in the same channel, by sequentially alternating the reference solutions with the unknown test samples. Analogous to the idea of bracketing the unknown samples in space at the same time, this idea is to bracket the unknown samples in time, at the same location.

Optionally, in this embodiment, the sequential temperature reference material boluses may serve a dual purpose. For example, if used in conjunction with a flowing real-time PCR system (see U.S. Patent Application Publication No. 2008/0003588, incorporated herein by reference), these temperature reference material boluses could also be used as flow markers to measure the flow rate and/or dispersion along a channel.

In another embodiment, the temperature reference materials are used to bracket unknown DNA sample boluses in both space and time. In other words, the previous embodiments are combined and used together.

In another embodiment, the temperature references are mixed into the unknown DNA sample. This method could be the ultimate in accuracy because the temperature reference is measured in the same location and at the same time as the unknown sample. This method requires the use of a material whose optical property change with temperature is discernible from the melt-dependent fluorescence from the DNA/binding dye under test. There are a number of physical properties that could conceivably be measured including absorbance and luminescence the efficiency, wavelength, polarization, or lifetime of emitted fluorescence; absorbance vs. wavelength, birefringence, etc. The addition of the temperature standard would ideally not interfere with the DNA melt measurement in any way, i.e. it would not alter the melt properties, would not affect the measurement process, and also would preferably not interfere with PCR.

In another embodiment, the optical signature from a temperature reference material is used to provide feedback to the heater, allowing for more accurate temperature control at that location.

Examples of the present invention (of the many embodiments and modes of operation) in which the container is a planar microfluidic chip with one or more microchannels are illustrated in FIGS. 4-7. Boluses of PCR products (DNA sample or test boluses) to be tested by melt curve analysis flow through these channels at a steady rate. These examples illustrate examples in which DNA sample boluses are alternated or combined with temperature reference material boluses in a microfluidic channel. In each example, fluorescence signals from DNA melting or signals from the temperature reference material are collected. This process may be repeated many times without physically moving or replacing the microfluidic chip. Data from temperature reference materials are used to determine spatial temperature gradients. Data from temperature references at different times (i.e. Melt 1 vs. Melt 2) are used to determine if temporal fluctuations have occurred.

Figure 4:
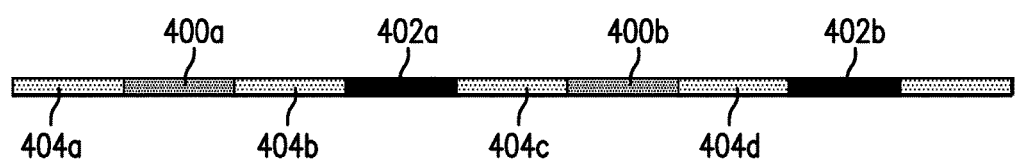
FIG. 4 is a diagram illustrating the spatial relationship of a DNA sample and a temperature reference material according to an embodiment of the present invention.

FIG. 4 illustrates an example of the present invention in which a test bolus containing DNA to be analyzed (400*a*, 400*b*) alternates with a temperature reference bolus (402*a*, 402*b*). Each test bolus and each temperature reference bolus are separated by spacer fluid (404*a*, 404*b*, 404*c*, 404*d*).

Figure 5:
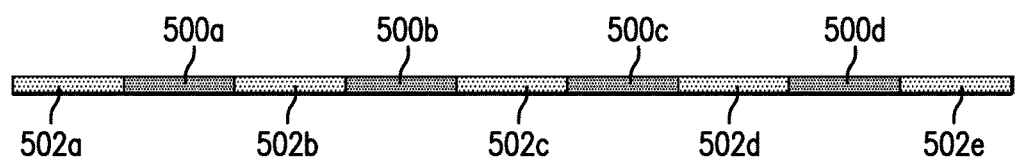
FIG. 5 is a diagram illustrating the spatial relationship of a DNA sample and a temperature reference material according to another embodiment of the present invention.

FIG. 5 illustrates an example of the present invention in which a test bolus containing DNA to be analyzed (500*a*, 500*b*, 500*c*, 500*d*) alternates with a bolus that contains a combined flow marker and a temperature reference material (502*a*, 502*b*, 502*c*, 502*d*, 502*e*).

Figure 6:
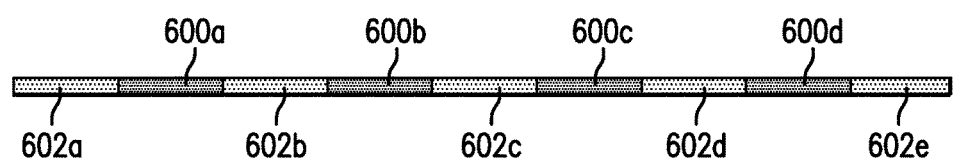
FIG. 6 is a diagram illustrating the spatial relationship of a DNA sample and a temperature reference material according to an additional embodiment of the present invention.

FIG. 6 illustrates an example of the present invention in which a test bolus contains both the DNA to be analyzed and the temperature reference material (600*a*, 600*b*, 600*c*, 600*d*). The test boluses are separated by spacer fluid (602*a*, 602*b*, 602*c*, 602*d*, 602*e*).

Figure 7:
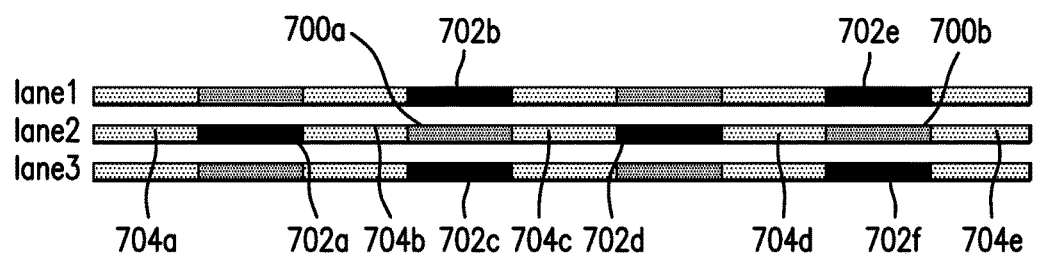
FIG. 7 is a diagram illustrating the spatial relationship of a DNA sample and a temperature reference material according to a further embodiment of the present invention.

FIG. 7 illustrates an example of the present invention in which the microfluidic chip contains three channels (lanes 1-3). A test bolus containing DNA to be analyzed (700*a*, 700*b*) is bracketed by boluses that contain a combined flow marker and temperature reference material (702*a*, 702*b*, 702*c*, 702*d*, 702*e*, 702*f*). The test boluses and the temperature reference boluses in the same channel are separated by spacer fluid (704*a*, 704*b*, 704*c*, 704*d*, 704*e*).

Figure 8:
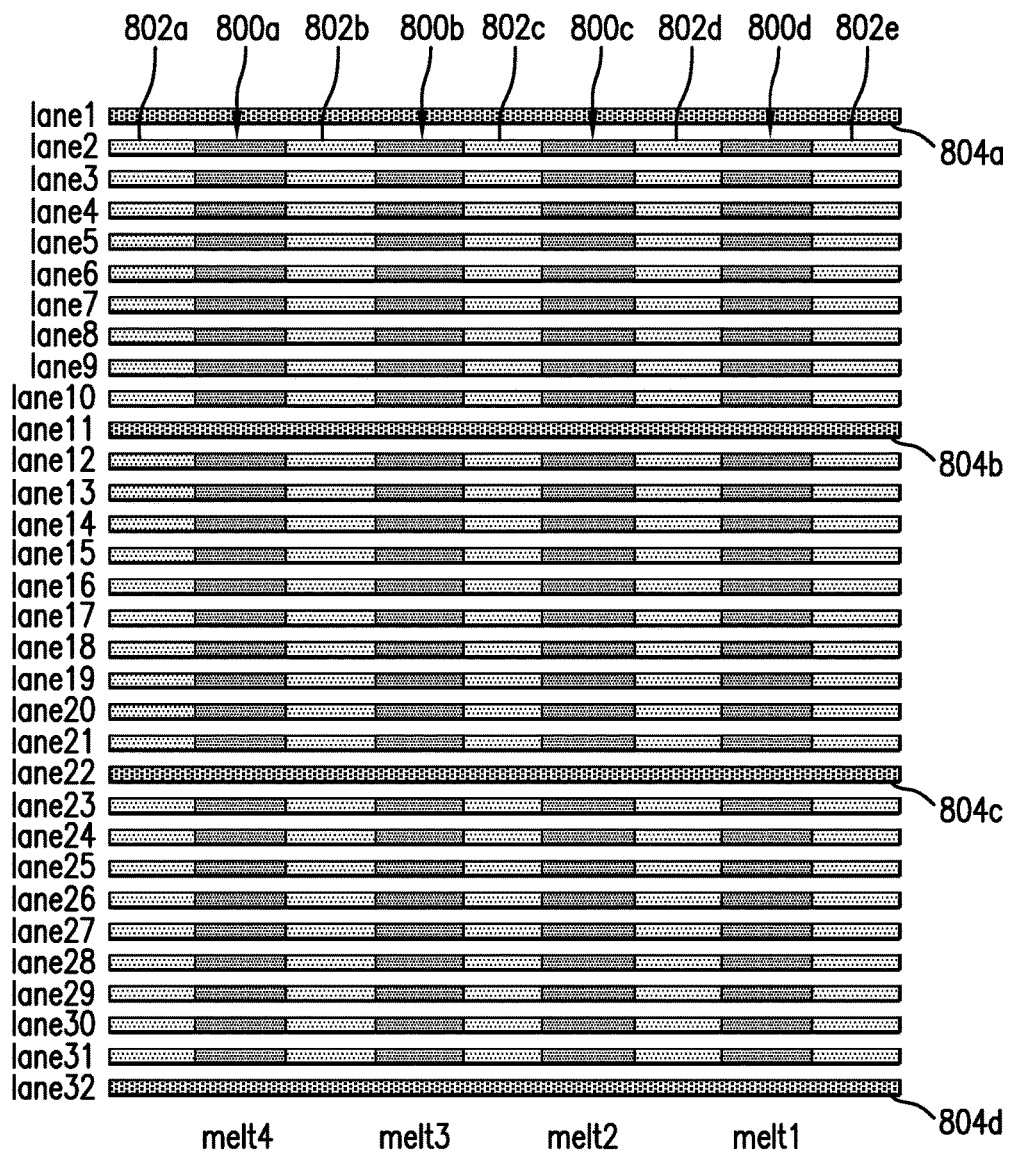
FIG. 8 is a diagram illustrating the spatial relationship of a DNA sample and a temperature reference material according to another embodiment of the present invention.

FIG. 8 illustrates an example (of the many embodiments and modes of operation) in which the container is a planar microfluidic chip with 32 parallel microchannels (lanes 1-32). Boluses of PCR products (DNA sample boluses) (800*a*, 800*b*, 800*c*, 800*d*) to be tested by melt curve analysis flow through these channels at a steady rate, alternating with a spacer fluid (802*a*, 802*b*, 802*c*, 802*d*, 802*e*). Some of the channels (e.g., lanes 1, 11, 22, and 32 as shown in this illustration) contain a temperature reference material (804*a*, 804*b*, 804*c*, 804*d*). As a first group of DNA sample boluses reaches the melt zone, all 32 channels are subjected to the temperature ramp (Melt 1) while fluorescence signals from DNA melting and signals from the temperature reference material are collected from all the lanes. Later, when the second group of DNA sample boluses reaches the melt zone detector, the melt measurement is performed again (Melt 2). This process may be repeated many times (Melt 3, 4, etc.) without physically moving or replacing the microfluidic chip. Data from temperature reference materials measured simultaneously at different locations are used to determine spatial temperature gradients. Data from temperature references at different times (i.e. Melt 1 vs. Melt 2) are used to determine if temporal fluctuations have occurred.

As evident from the above description, the present invention provides ways to reduce the impact of temperature gradients and fluctuations in a system for melt curve data collection.

By keeping the chamber in close thermal contact and with proper geometry of the heater, instantaneous temperature differences between chambers is kept small.

Using data from a temperature reference inside a chamber located near to the sample chamber, rather than a temperature sensor external to the container (which may experience significant temperature offsets due to the dynamic nature of the temperature ramp) could provide a more accurate and precise estimate of the temperature in the sample chamber.

Using data from more than one temperature reference inside spatially separated chambers provides information on the magnitude of temperature gradients and may allow one to more precisely estimate the temperature at other locations.

Using a refillable chamber (e.g, via a microcapillary tube or microfluidic channel) allows one to test different solutions without moving the container, which could alter the properties of the temperature control and measurement system or the optical measurement system. This should result in greater reproducibility from measurement to measurement.

By measuring temperature reference materials sequentially in the same chamber as the DNA test samples, one has the ability to monitor the degree of temperature fluctuations between measurements over the course of minutes.

By mixing a temperature reference material directly into the DNA sample bolus and measuring both simultaneously at the same location, errors due to gradients and temporal fluctuations may be eliminated. This requires a reference material that does not interfere with the DNA melt measurement or other processes.

The above methods used alone or in combination would enhance the usefulness of the melt curve analysis technique by improving the accuracy and reliability of the temperature measurement.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A system for performing melt curve data collection comprising:
    a container comprising at least three chambers, wherein at least two of the chambers are spatially separated from each other, and contain a temperature reference material, and at least one chamber contains a DNA test sample;
    a heating system to heat the container;
    a detection system, wherein a detectable signal from the temperature reference material provides feedback to the heating system; and
    a control system for determining a spatial temperature gradient due to temporal fluctuation within the container to calculate a temperature at a location of the DNA test sample based on temperature results from the temperature reference material that surrounds the location of the DNA test sample.

2. The system of claim 1, wherein the heating system supplies heat to all of the chambers simultaneously.

3. The system of claim 1, wherein the chambers contain at least two spatially separated temperature reference materials to determine a spatial temperature gradient.

4. The system of claim 1, wherein the temperature reference material brackets the DNA test sample in both space and time.

5. The system of claim 1, wherein the temperature reference material is mixed with the DNA test sample.

6. The system of claim 1, wherein the detection system is an optical detection system.

7. The system of claim 1, wherein the container is a microfluidic chip and the chambers are microfluidic channels in the chip.

8. The system of claim 1, wherein at least two chambers containing DNA test samples are located between two chambers containing the temperature reference material.

9. The system of claim 1, wherein the temperature reference material is a known DNA mixture.

10. The system of claim 1, wherein the temperature reference material is a thermochromatic material.

11. A system for performing melt curve data collection, said system comprising:
    a container comprising at least three chambers that are refillable without moving the container, wherein at least two of the chambers are spatially separated from each other and contain a temperature reference material, and at least one chamber contains a DNA test sample;
    a heating system to heat the container;
    a detection system, wherein a detectable signal from the temperature reference material provides feedback to the heating system;
    a control system for determining a spatial temperature gradient due to temporal fluctuation within the container to calculate a temperature at a location of the DNA test sample based on temperature results from the temperature reference material that surrounds the location of the DNA test sample.

12. The system of claim 11, wherein the heating system supplies heat to all of the at least three chambers simultaneously.

13. The system of claim 11, wherein the detection system is an optical detection system.

14. The system of claim 11, wherein the DNA test sample and the temperature reference material are alternated in the chamber.

15. The system of claim 11, wherein the temperature reference material brackets the DNA test sample in both space and time.

16. The system of claim 11, wherein the DNA test sample and the temperature reference material are mixed, wherein the temperature reference material has a detection signature that is discernible from that of the DNA test sample, and wherein data from both the sample and the temperature reference material are collected at the same place and the same time.

17. The system of claim 11, wherein the temperature reference material is also a flow marker.

18. The system of claim 11, wherein at least two chambers containing DNA test samples are located between two chambers containing the temperature reference material.

19. The system of claim 11, wherein the temperature reference material is a known DNA mixture.

20. The system of claim 11, wherein the temperature reference material is a thermochromatic material.

21. The system of claim 1, wherein at least two of the chambers are located less than 1 mm from each other.

22. The system of claim 1, wherein the detection system monitors optical properties from the chambers simultaneously.

23. The system of claim 11, wherein at least two of the chambers are located less than 1 mm from each other.

24. The system of claim 11, wherein the detection system monitors optical properties from the chambers simultaneously.

* * * * *